United States Patent [19]

Steiger et al.

[11] Patent Number: 5,285,692
[45] Date of Patent: Feb. 15, 1994

[54] METHODS FOR MEASURING PHYSICAL PARAMETERS OF A LOW PERMEABILITY ROCK FORMATION IN SITU

[75] Inventors: Ronald P. Steiger, Houston; Peter K. Leung, Sugar Land, both of Tex.

[73] Assignee: Exxon Production Research Company, Houston, Tex.

[21] Appl. No.: 931,865

[22] Filed: Aug. 18, 1992

Related U.S. Application Data

[62] Division of Ser. No. 577,337, Aug. 31, 1990, Pat. No. 5,205,164.

[51] Int. Cl.$^5$ .............................................. G01N 3/00
[52] U.S. Cl. ....................................... 73/866; 73/597
[58] Field of Search ...................... 73/152, 153, 38, 39, 73/866

[56] References Cited

U.S. PATENT DOCUMENTS

| | | | |
|---|---|---|---|
| 3,199,341 | 8/1965 | Heuer, Jr. et al. | 73/820 |
| 3,421,366 | 1/1969 | Ely | 73/819 |
| 3,423,994 | 1/1969 | Scott et al. | 73/819 |
| 3,423,995 | 1/1969 | Scott et al. | 73/819 |
| 3,457,777 | 7/1969 | Nielsen | 73/84 |
| 3,505,860 | 4/1970 | Bishop et al. | 73/819 |
| 3,610,032 | 10/1971 | Di Crispino | 73/819 |
| 3,616,685 | 11/1971 | Strom | 73/819 |
| 3,635,078 | 1/1972 | Wissa | 73/89 |
| 3,728,895 | 4/1973 | Shaw | 73/94 |
| 3,820,385 | 6/1974 | Cordoba | 73/84 |
| 3,881,345 | 5/1975 | Souder | 73/94 |
| 3,975,950 | 8/1976 | Erdei | 73/94 |
| 4,201,082 | 5/1980 | Dockhorn et al. | 73/153 |
| 4,408,486 | 10/1983 | Rochon et al. | 73/155 |
| 4,430,890 | 2/1984 | Hains | 73/147 |
| 4,487,056 | 12/1984 | Wiley | 73/38 |
| 4,502,338 | 3/1985 | Smith et al. | 73/819 |
| 4,506,542 | 3/1985 | Rose | 73/38 |
| 4,561,289 | 12/1985 | Jones | 73/38 |
| 4,562,726 | 1/1986 | Barnaby | 73/38 |
| 4,587,857 | 5/1986 | Bush | 73/863 |
| 4,599,891 | 7/1986 | Brauer et al. | 73/38 |
| 4,607,532 | 8/1986 | Arthur et al. | 73/819 |
| 4,627,270 | 12/1986 | Jones | 73/38 |
| 4,631,677 | 12/1986 | Park et al. | 364/422 |
| 4,638,447 | 1/1987 | Odeh | 364/556 |
| 4,643,019 | 2/1987 | Jones | 73/38 |

(List continued on next page.)

OTHER PUBLICATIONS

Drilling Fluids, EPR Co., 1989.
Acoustical Properties of Clay Bearing Rocks, C. A. Tosaya, 1982.
Quantitative Determination of Mechanical Properties of Shales, Steiger & Leung, SPE Conf., Oct. 2-5, 1988.
"Predictions of Wellbore Stability In Shale Formations At Great Depth," Steiger and Leung, SPE Symposium 1989.
"The Mechanics of Soils," Atkinson et al. 1978, pp. 118-144, 184-209, 292-343.
"Soil Mechanics," Lambe et al., 1969, Chapter 20, pp. 295-303.

Primary Examiner—Donald O. Woodiel
Assistant Examiner—R. Biegel
Attorney, Agent, or Firm—Guy McClung

[57] ABSTRACT

A method for determining drilling fluid density for stabilizing a wellbore including obtaining shale cuttings from a wellbore. In one embodiment of a method according to this invention, shale cuttings are obtained from a wellbore and their index properties, including but not limited to surface area, is measured; mean effective stress around the wellbore is calculated using the geostatic overburden in situ stress, the field pore pressure, and the total stress around the wellbore; the in situ shale strength is determined using a correlation between surface area, mean effective stress and shale strength; and drilling fluid density is determined using the shale strength. Methods for determining in situ shale strengths, elastic properties, pore pressures, and formation stresses of low permeability rocks.

4 Claims, 5 Drawing Sheets

U.S. PATENT DOCUMENTS

| | | | |
|---|---|---|---|
| 4,648,261 | 3/1987 | Thompson et al. | 73/38 |
| 4,649,737 | 3/1987 | Jones | 73/38 |
| 4,669,299 | 6/1987 | Closmann | 73/38 |
| 4,679,421 | 7/1987 | Barree | 73/38 |
| 4,679,441 | 7/1987 | Johnson et al. | 73/798 |
| 4,694,692 | 9/1987 | Brown et al. | 73/153 X |
| 4,710,948 | 12/1987 | Withjack | 378/208 |
| 4,715,212 | 12/1987 | Johanson | 73/38 |
| 4,753,107 | 6/1988 | Reed et al. | 73/38 |
| 4,762,003 | 8/1988 | Cioletti | 73/825 |
| 4,791,822 | 12/1988 | Penny | 73/865 |
| 4,799,382 | 1/1989 | Sprunt et al. | 73/153 |
| 4,807,465 | 2/1989 | Botzolakis et al. | 73/78 |
| 4,825,700 | 5/1989 | Vardoulakis et al. | 73/749 |
| 4,827,761 | 5/1989 | Vinegar et al. | 73/38 |
| 4,845,995 | 7/1989 | Kaste et al. | 73/794 |
| 4,848,145 | 7/1989 | Blaschke et al. | 73/153 |
| 4,856,341 | 8/1989 | Vinegar et al. | 73/798 |
| 4,864,846 | 9/1989 | Jones | 73/38 |
| 4,868,751 | 9/1989 | Dogru et al. | 364/422 |
| 4,879,654 | 11/1989 | Bruce | 73/434 X |
| 4,884,438 | 12/1989 | Jones et al. | 73/153 |
| 4,885,941 | 12/1989 | Vardoulakis et al. | 73/794 |
| 4,955,237 | 9/1990 | Suzuki et al. | 73/784 |
| 4,957,001 | 9/1990 | Powell | 73/716 |
| 4,961,343 | 10/1990 | Boone | 73/152 |
| 5,018,396 | 5/1991 | Penny . | |
| 5,025,668 | 6/1991 | Sarda et al. . | |
| 5,025,669 | 6/1991 | Sarda et al. . | |

METHODS FOR MEASURING PHYSICAL PARAMETERS OF A LOW PERMEABILITY ROCK FORMATION IN SITU

This is a division of pending U.S. application Ser. No. 07/577,337 filed on Aug. 31, 1990 entitled "Methods For Determining In Situ Shale Strengths, Elastic Properties, Pore Pressures, Formation Stresses, and Drilling Fluid Parameters" now U.S. Pat. No. 5,205,164.

BACKGROUND OF THE INVENTION

1. Field of the Invention

This invention is directed to methods for determining the in situ strengths, pore pressures, elastic properties and formation stresses, of low permeability rocks such as shales and for determining desired parameters for fluids used in drilling wellbores.

2. Description of Related Art

Subsurface formations encountered in oil and gas drilling are compacted under in situ stresses due to overburden weight, tectonic effects, confinement and pore pressure. When a hole is drilled in a formation, the wellbore rock is subjected to increased shear stresses due to a reduction in confinement at the wallbore face by removal of the rock from the hole. compressive failure of the rock near the wellbore will occur if the rock does not have sufficient strength to support the increased shear stresses imposed upon it. However, if the hole is filled with drilling fluid with sufficient density (mud weight) to increase the wellbore pressure or confining pressure to a proper level, the shear stresses imposed on the wellbore rock will be reduced and the hole will remain stable. If the wellbore pressure is increased too much, lost circulation or hydraulic fracturing of the formation will occur as a result of tensile failure of the wellbore rock.

Classical elastic and elasto-plastic theories, failure criteria and fracture mechanics have been applied to model wellbore behavior under different stress conditions. An elastic model has been used with stress, pore pressure and empirically derived rock strength values to predict wellbore behavior. One of the present inventors has modeled the behavior of high angle wells in the North Sea by using classical theories and stress, pore pressure and empirically derived shale strength data from several of the early wells. The model results provided wellbore stability charts that showed the proper wellbore pressures or equivalent drilling mud weights or densities required to prevent wellbore collapse and lost circulation as a function of hole angle and depth. The wellbore stability charts were used as engineering guidelines for subsequent wells and saved many millions of dollars by reducing trouble costs due to wellbore failure. Examples of the wellbore stability charts for 0, 45 and 60 degree wells are given in FIG. 1. However, these drilling guidelines were developed at the expense of many stuck pipe incidents and other wellbore stability-related hole problems. Many millions of dollars of drilling trouble costs were spent before the rock strengths were determined empirically. This example and subsequent cases showed that if shale strength data were available a wellbore model could be used on initial wells in an area to diagnose and predict wellbore behavior and to prevent expensive stuck pipe problems and high trouble costs. Others recognized the importance of this approach and emphasized the need for shale strength data.

Some shales at great depths can be overcompacted and show peak stress behavior during triaxial tests. Complete stress-strain measurements past the peak stress to residual or ultimate stresses were obtained under pore pressure equilibrium conditions for each of several low permeability shales. An example of complete stress-strain curves for a low permeability shale is given in FIG. 2. Failure criteria or shear strength versus mean effective stress relationships were determined for the shales for both peak stress and residual or ultimate stress. An example of a failure criterion for a low permeability shale is shown in FIG. 3. This mean effective stress and strength relationship is frequently referred to as a Drucker-Pager model or an extended Von Mises criterion. Other failure relationships could also be used, e.g. Mohr-Coulomb and critical state.

The total specific surface area of a shale has been interpreted to be a quantitative measure of the hydratable surfaces present in the shale and an indicator of the hydratable clays present in the rock. The presence of hydratable clays affect the mechanical properties of the rock. One of the co-inventors of the present invention used the total specific surface area (or specific surface) as a means to classify different types of shales since it was found that in general those with high surface areas tended to be weak rocks (under similar stress environments) that produced wellbore failure under low to moderate stress conditions and that low surface area shales tended to be much stronger rocks.

In addition, one of the co-inventors found an empirical relationship that showed that shales with higher surface areas required higher concentrations of chemical inhibitors, e.g. potassium ions, in a drilling fluid to minimize shale hydration and weakening of the formation. The empirical surface area-inhibitor concentration relationship has been used to determine the optimum inhibitor, e.g. potassium chloride concentration required in a drilling fluid to minimize hydration and weakening of a shale formation with a certain surface area.

SUMMARY OF THE PRESENT INVENTION

According to the methods of the present invention, shale core samples are obtained from a wellbore and their specific surface areas are measured directly; e.g., but not limited to, the DCM method of U.S. Pat. No. 4,876,512. Then, shale strengths or failure criteria for each shale type [as described in the co-pending, co-owned application entitled "Methods and Apparatuses For Measurement of the Strengths, Pore Pressures, and Mechanical Properties of Low Permeability Geologic Materials, naming one of the present inventors as inventor] are measured. FIG. 9 shows the strength-mean effective stress relationship (Drucker-Prager) for different shales with different surface areas. Shale C is a high surface area shale; Shale B, medium surface area; and Shale A, low surface area. Shale strength data for the different shales tested are correlated with their total specific surface areas and a relationship between peak shale strength, mean effective stress ($\sigma'$), and a shale index property, e.g. total specific surface area (S.A.) is demonstrated; for example, shale strength = f(S.A., $\sigma'$).

This correlation is used to determine general estimates of in situ shale strengths for engineering design from in situ stress data, pore pressure data and index properties, e.g. surface area measurements, on drill cuttings; and in one embodiment cuttings from the first well in an area yield data applicable to subsequent wells.

These strength values are used to determine the lowest drilling fluid density or mud weight that would be required to stabilize a particular shale if it was overcompacted. The shale strength correlations can be used at a rig site to predict stable wellbore conditions. A correlation is then also made between the residual or ultimate shale strength, mean effective stress, and total specific surface area for each shale. This correlation is used to determine an in situ shale strength value for a very conservative or worst case engineering design. These strength values can be considered critical state values or values independent of stress path considerations. They are also useful to determine the lowest drilling fluid density or mud weight ("fracturel" or "maximum") that would be required to stabilize a particular shale if it were a normally compacted or undercompacted shale. The shale strength correlations can be used at a rig site to predict stable wellbore conditions.

The present inventors along with others, developed the prior art rig-site method, based on dielectric constant measurements (described in U.S. Pat. No. 4,876,512), to measure the surface area of drill cuttings ("DCM method"). Surface area data from this method can be quickly measured at the rig while drilling a well.

If hole problems develop in a particular shale at a certain depth, the shale cuttings are analyzed using the DCM method and the surface area (index property) value is used to determine the strength of the shale from the shale strength correlation curves (e.g. FIGS. 4 and 5) that are developed by the present method. The shale strength is compared with the wellbore stresses at that depth. If the strength is found to be higher than the wellbore shear stresses, a stable condition against wellbore collapse or compressive failure exists. If the strength is lower than the wellbore stresses, an unstable or compressive failure condition exists. Calculations are made to determine the proper equivalent drilling mud weight or wellbore pressure that will reduce the wellbore stresses to a value lower than the strength of the shale or that provides a stable wellbore condition.

Other shale strength-mean effective stress-index property correlations according to the present invention can be based on other index properties; e.g. x-ray diffraction data, compositional data, cation exchange capacity data, ultrasonic velocity data, Atterberg limits, or other clay content related physical or chemical measurements on a few typical shales.

In one embodiment, the strengths, mean effective stress, and an index property (e.g., physical or chemical property values or values derived therefrom) are measured for each of several shales. Then a mathematical function is determined that gives a best fit for all the data. Thus, if a mathematical function that relates shale strength, effective stress and, e.g., cation exchange capacity (CEC) is determined from measurements on several shales, then only the CEC of a field shale sample needs to be measured and combined with the given effective stress to calculate the strength of the shale sample in that downhole effective stress environment. In one embodiment, the surface area index property of a shale sample is determined using the DCM method and the value is used to determine the potassium chloride (KCl) inhibitor concentration (as in the prior art) required in a drilling fluid to minimize hydration and weakening of the shale. The surface area index property value is then also used with the predetermined correlation between shale strength means effective stress and surface area to determine the in situ shale strength. FIG. 10 presents schematically such a method. It shows the measurement of a shale's dielectric constant yielding its surface area. The surface area yields a preferred KCl concentration and, combined with a Mean effective stress, the shale strength.

In one embodiment of a method according to this invention, shale cuttings are obtained from a wellbore and their surface area is measured or determined; mean effective stress around the wellbore is calculated using the geostatic overburden in situ stress, the field pore pressure, and the total stress around the wellbore; the in situ shale strength is determined using a correlation between Mean effective stress and shear strength; and drilling fluid density is determined using the in situ shale strength. Embodiments of this method are described in detail below.

It was also found that a modification to the ethylene glycol monoethyl ether (EGME) surface area method for soils by Cartor et al. worked well in the laboratory for compacted shales and could be run on a small amount of drill cuttings.

Appended hereto and included herein for all purposes are copies of the following applications, filed on even date herewith, and co-owned with this application:

"Methods And Apparatuses For Measurement Of The strengths, Pore Pressures, And Mechanical Properties of Low Permeability Geologic Materials," naming Mr. Ronald P. steiger as inventor.

"Apparatuses And Methods For Adjusting A Material's Fluid content And Effective Stresses," naming Messrs. Ronald P. Steiger and Peter K. Leung as co-inventors.

"Apparatuses and Methods For Measuring Ultrasonic Velocities In Materials," naming Messrs. Ronald P. steiger and Peter K. Leung as co-inventors.

"Microaccumulator For Measurement Of Fluid Volume Changes Under Pressure" naming Messrs. Ronald P. Steiger, Peter K. Leung, and Rudolf J. Stankovich as inventors.

For example, a well is drilled vertically to 10,000 feet. The vertical stress is 9,900 p.s.i. and the two horizontal stresses are 7,800 p.s.i. The pore pressure is 5,500 p.s.i. The shale surface area calculated based on dielectric constant measurement of a shale cuttings sample from a 10,000 foot depth is 200 $m^2$/gm. Using the wellbore stress equations provided herein, the mean effective stress around the wellbore is 3,000 p.s.i. with surface area = 200 $m^2$/gm and mean effective stress = 3,000 p.s.i., the in situ strength of the formation at 10,000 feet TVD is estimated to be 1,888 p.s.i. The strength estimate is obtained from the correlation shown in FIG. 4.

It is, therefore, an object of the present invention to provide new, useful, unique, efficient, effective and nonobvious methods for determining in situ shale strengths, elastic properties, pore pressures, and formation stresses; and methods for determining an appropriate drilling fluid parameters.

To one of skill in this art who has the benefits of this invention's teachings and disclosures, other and further objects and advantages will be clear, as well as others inherent therein, from the following description of presently preferred embodiments, given for the purpose of disclosure, when taken in conjunction with the accompanying drawings. Although these descriptions are detailed to insure adequacy and aid understanding, this is not intended to prejudice that purpose of a patent which is to claim an invention no matter how others may later disguise it by variations in form or additions of further improvements.

DESCRIPTION OF THE DRAWINGS

So that the manner in which the above-recited features, advantages and objects of the invention, as well as others which will become clear, are attained and can be understood in detail, more particular description of the invention briefly summarized above may be had by reference to certain embodiments thereof which are illustrated in the appended drawings, which drawings form a part of this specification. It is to be noted, however, that the appended drawings illustrate preferred embodiments of the invention and are therefore not to be considered limiting of its scope, for the invention may admit to other equally effective equivalent embodiments.

DESCRIPTION OF EMBODIMENTS PREFERRED AT THE TIME OF FILING FOR THIS PATENT

Figure 6:
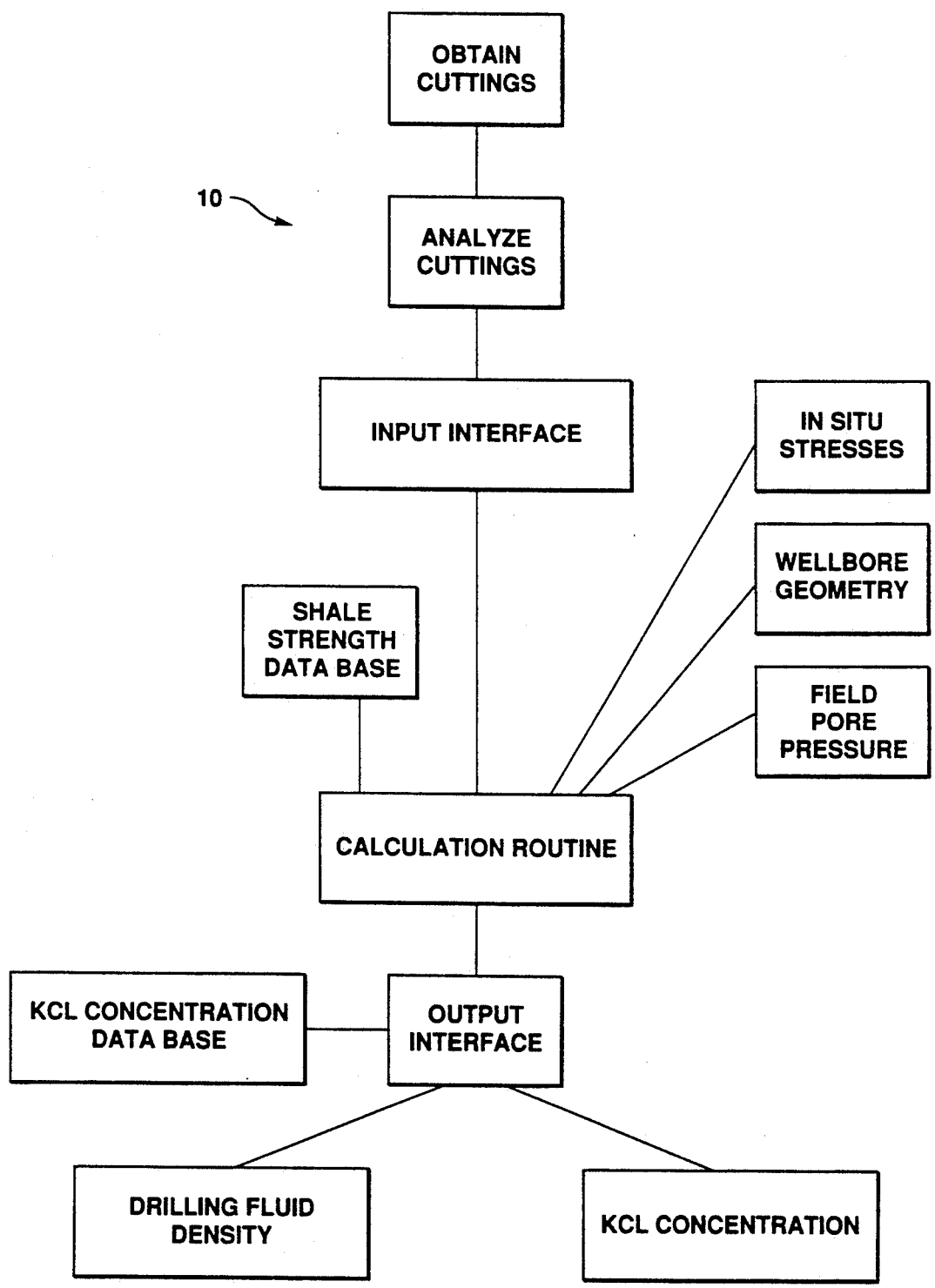
FIG. 6 is a flow chart of a method according to the present invention.

A method 10 according to the present invention is represented schematically in FIG. 6. According to this method, shale cuttings are obtained ("OBTAIN CUTTINGS") from a wellbore and their surface area is measured or determined ("ANALYZE CUTTINGS"). One way to determine surface area, presented in U.S. Pat. No. 4,876,512 co-owned with this application and fully incorporated herein, includes measuring the dielectric constant of a shale and then determining its surface area.

From typical sources, e.g. density logs and extended leak off tests, in situ geostatic stresses are determined ("IN SITU STRESSES"). Density log data is used to calculate a vertical stress component and extended leak off test data is used to calculate a horizontal stress component. These two components are then used to calculate the total in situ stress.

From typical sources, e.g. mud logging reports, and well data from other wells, data are obtained for calculating field pore pressure ("FIELD PORE PRESSURE"). The wellbore geometry ("WELLBORE GEOMETRY") (depth, dimension, direction) is obtained from conventional sources, e.g. such as well survey data. Using conventional methods, e.g. linear elastic equations, total stress around the wellbore is calculated.

["CALCULATION ROUTINE"] By subtracting the field pore pressure from this total stress, the mean effective stress around the wellbore is determined. ["CALCULATION ROUTINE"]

By using correlations of mean effective stress and shale shear strength (determined from a shale strength data base for shales from, e.g., data derived from tests according to the four-previously described and appended co-pending applications) the in situ strength of the shale under study is determined ("CALCULATION ROUTINE"). Equations shown below for exemplary calculations are used in correlating stress and strength.

It is preferred, but not necessary, that KCl (potassium chloride) concentration ("KCL concentration data base") be one parameter determined with this method ("calculation routine"). Such determinations are known in the prior art.

Using the total wellbore stress, the mean effective stress around the wellbore, and in situ shale shear strength, failure criteria are defined for the shale under study ("CALCULATION ROUTINE"); i.e., the strength less than which the shale will fail is determined. Then, using an iterative process described in detail below, an appropriate drilling fluid density is determined ("CALCULATION ROUTINE"). Also, KCl concentration is calculated.

A typical method according to this invention includes the following steps (assume Poisson's Ratio=0.4):

1. calculate depth from the mud line (MdLnDpt) (e.g. from the seafloor):

$MdLnDpt = TVD - WtrDpt$

Where, WtrDpt = Water Depth

On land, Wtr Dpt = 0

TVD = True Vertical Depth

2. Calculate hole direction in relation to Maximum Horizontal Stress (MaxHrzlstrs):

$Beta = abs (WlbrAzm - MaxHrzlstrsAzm)$

Alpha = Wellbore drift or angle

[WlbrAzm = Wellbore Azimuth;
    MaxHrzlstrsAzm = Azimuth of the maximum horizontal stress]

3. Convert in-situ stress gradient to total stress:

Sigma1 = Ovrbdstrsgrdn (Overburden stress gradient) * MdLnDpt

Sigma2 = MaxHrzlStrsGrdn (Maximum horizontal stress gradient) * MdLnDpt

Sigma3 = MinHrzlStrsGrdn (Minimula horizontal stress gradient) * MdLnDpt

PorePrsr = PorePrsrGrdn (Pore pressure gradient)* MdLnDpt

4. Transform stresses in (Sigma 1,2,3) coordinates into new local coordinate relative to the hole (x,y,z) yielding new coordinates in x,y,z system:

$$Sigmax = Sigma3 * Cos^2(Beta) + Sigma2 * Sin^2 (Beta)$$

$$Sigmay = (Sigma3 * Sin^2 (Beta) + Sigma2 * Cos^2 (Beta)) * Cos^2 (Alpha) + Sigma1 Sin^2 (Alpha)$$

$$Sigmaz = (Sigma3 * Sin^2 (Beta) + Sigma2 * Cos^2 (Beta)) * Sin^2 (Alpha) + Sigma1 * Cos^2 (Alpha)$$

$$Tauxy = 0.5 (Sigma2 - Sigma3) * Sin (2 * Beta) * Cos (Alpha)$$

$$Tauyz = 0.5 * (Sigma1 - Sigma3) * Sin^2 (Beta) - Sigma2 * Cos^2 (Beta)) * Sin (2 * Alpha)$$

$$Tauxz = 0.5 * (Sigma2 - Sigma3) * Sin (2 * Beta) * Sin (Alpha)$$

5. Calculate surface area:
   a. DCM (dielectric constant measurement yields DCM) option (U.S. Pat. No. 4,876,512)

$$SurfArea = 0.0331 * DCM^2 + 2.19 * DCM - 45.92$$

b. Direct measurement [e.g. EGME method]
6. Calculate Poisson ratio (PssnRt):

$$PssnRt = f (SurfArea; \text{ mean effective stress})$$

7. Set Theta (angle around wellbore) to zero degree
8. Calculate effective confining stress (EffStrs) as a function of Theta:

$$A1 = Sigmax + Sigmay$$

$$A2 = 2 * (Sigmax - Sigmay) * Cos (2 Theta)$$

$$A3 = 4 * Tauxy * Sin (2 * Theta)$$

$$c = Sigmaz - PssnRt * (A2 + A3)$$

$$d = A1 - A2 - A3$$

$$EffStrs = (c + d)/3 - PorePrsr$$

[PorePrsr = in situ pore pressure of the formation]

9. Calculate rock strength (Rock Strgh):

$$RockStrgh = \exp(\exp(2.638281 - (.1459 * \ln(SurfArea)))) + ((Effstrs * (.605 - (.00094 * SurfArea))))$$

[e.g. $\exp^2$ means $e^2$; $\exp^{expr}$ means $e^{expr}$]
[ln = log]

10. Calculate collapse mud weight (ClpMW):

$$Tauzt = 2 * (Tauyz * Cos (Theta) - Tauxz * Sin (Thota))$$

$$b1 = 9 * d^2 - 12 * (d^2 + c^2 - c * d - 4.5 \, RockStrgh^2 + 3 * Tauzt^2)$$

If $b1 > 0$ $b2 = $ square root (b1)

If $b1 < 0$ $b2 = $ "null"

$$ClpsMW = (3 * d - b2)/(6 * TVD * 0.052)$$

11. Calculate maximum allowable mud weight:

$$FracMW = (d - PorePrsr)/(TVD * 0.052)$$

[FracMW is the mud weight that will cause fracturing of the wellbore]

12. Increase Theta 5 degrees, 72 times, to 360 degree. For each increment, repeat steps 8-10 to obtain ClpsMW and FracMW. Find and save the maximum collapse MW and minimum fracture KW around the wellbore.

Tables I and II present input and output data for typical determinations using methods according to the present invention. Table I represents the following input data:

TABLE I

| A | B | C | D | E | F | G | H | I | J |
|---|---|---|---|---|---|---|---|---|---|
| | SURVEY | | | | STRESS | | | ROCK | |
| TVD ft | Drift Decimal | Azimuth Decimal | PorePrss psi/ft | OverBdn psi/ft | Mn Hz Grd psi/ft | Mx Hz Grd psi/ft | Mx Hz Azm Decimal | EGME m2/g | DCM |
| 5000.0 | 0.000 | 10.000 | 0.500 | 0.900 | 0.720 | 0.720 | 40.000 | 100.0 | 40.000 |
| 5500.0 | 15.000 | 15.000 | 0.500 | 0.900 | 0.720 | 0.720 | 40.000 | 125.0 | 44.000 |
| 6000.0 | 25.000 | 10.000 | 0.600 | 0.900 | 0.720 | 0.720 | 40.000 | 135.0 | 49.000 |
| 6500.0 | 30.000 | 19.000 | 0.625 | 0.900 | 0.720 | 0.750 | 40.000 | 160.0 | 55.000 |
| 7000.0 | 35.000 | 10.000 | 0.600 | 0.900 | 0.720 | 0.750 | 40.000 | 175.0 | 55.000 |
| 7500.0 | 45.000 | 0.000 | 0.500 | 0.900 | 0.720 | 0.800 | 40.000 | 135.0 | 43.000 |
| 8000.0 | 50.000 | 10.000 | 0.475 | 0.900 | 0.720 | 0.750 | 40.000 | 125.0 | 42.000 |
| 8500.0 | 60.000 | 5.000 | 0.437 | 0.900 | 0.720 | 0.720 | 40.000 | 115.0 | 39.200 |
| 9000.0 | 65.000 | 15.000 | 0.437 | 0.900 | 0.720 | 0.720 | 40.000 | 135.0 | 42.500 |
| 9500.0 | 75.000 | 10.000 | 0.437 | 0.900 | 0.720 | 0.720 | 40.000 | 95.0 | 42.500 |
| 10000.0 | 85.000 | 8.000 | 0.437 | 0.900 | 0.720 | 0.720 | 40.000 | 100.0 | 43.200 |
| 10500.0 | 90.000 | 9.000 | 0.437 | 0.900 | 0.720 | 0.720 | 40.000 | 70.0 | 30.100 |

TABLE II

| K | L | M | N | O |
|---|---|---|---|---|
| TVD ft | Minimum Mud Wt. ppg | Maximum Mud Wt. ppg | Estimated Min KCl ppb | Estimated Max KCl ppb |
| 5000.0 | 4.7 | 23.0 | 20.6 | 31.3 |
| 5500.0 | 6.9 | 21.4 | 24.3 | 37.1 |
| 6000.0 | 9.5 | 18.5 | 25.8 | 39.4 |
| 6500.0 | 11.3 | 16.9 | 29.6 | 45.2 |
| 7000.0 | 11.9 | 17.0 | 31.9 | 48.6 |
| 7500.0 | 10.3 | 19.5 | 25.8 | 39.4 |
| 8000.0 | 10.0 | 19.2 | 24.3 | 37.1 |
| 8500.0 | 9.8 | 19.2 | 22.8 | 34.7 |
| 9000.0 | 10.8 | 18.4 | 25.8 | 39.4 |
| 9500.0 | 9.5 | 18.8 | 19.8 | 30.1 |
| 10000.0 | 10.0 | 18.3 | 20.6 | 31.3 |
| 10500.0 | 8.5 | 19.2 | 16.0 | 24.3 |

| Column | |
|---|---|
| A | Total vertical depth |
| B | Drift angle of the wellbore |
| C | Azimuth angle of the wellbore |
| D | In Situ Pore pressure of the rock |
| E | Overburden stress |
| F | Minimum horizontal stress gradient |
| G | Maximum horizontal stress gradient |
| H | Maximum horizontal stress azimuth |
| I | Rock surface area (EGME direct measurement method) or |
| J | Rock surface area (DCM method) |

[I in meters²/gram; J in microfarads; only one input value from either column I or J is required]

Table II presents the following output data:

| Column | |
|---|---|
| K | Total vertical depth |
| L | Collapse mud weight, i.e. minimum required mud weight to keep wellbore stable |
| M | Fracture mud weight, i.e. maximum mud weight the wellbore can take before fracture occurs |
| N | Minimum desirable KCL amount |
| O | Maximum desirable KCL amount |

Figure 7:
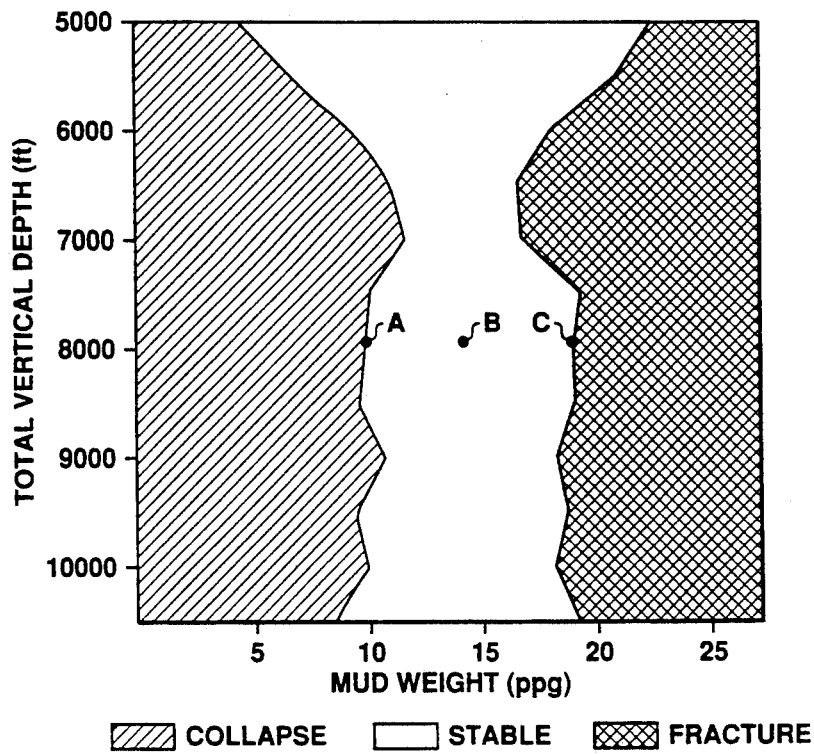
FIG. 7 is a graphical representation of results obtained utilizing methods according to the present invention.

FIG. 7 presents a graphic representation of desirable and undesirable drilling fluid (in this case mud) weights for a particular wellbore. The figure shows the combinations of mud weight and depth that results in compressive failure, stable conditions, or tensile failure. For example, three points at the same depth have been indicated in FIG. 7, points A, B and C. Point A represents the minimum mud weight that is needed to prevent wellbore collapse operation to the left of this point results in brittle or ductile collapse with the accompanying problems of tight holes, stuck pipe, etc. Point B is located in a stable region where compressive failure and lost circulation will not occur. Point C represents the maximum mud weight that the wellbore can take before lost circulations occur. Operation to the right of Point C causes the bore hole wall to fracture resulting in lost circulation.

Figure 8:
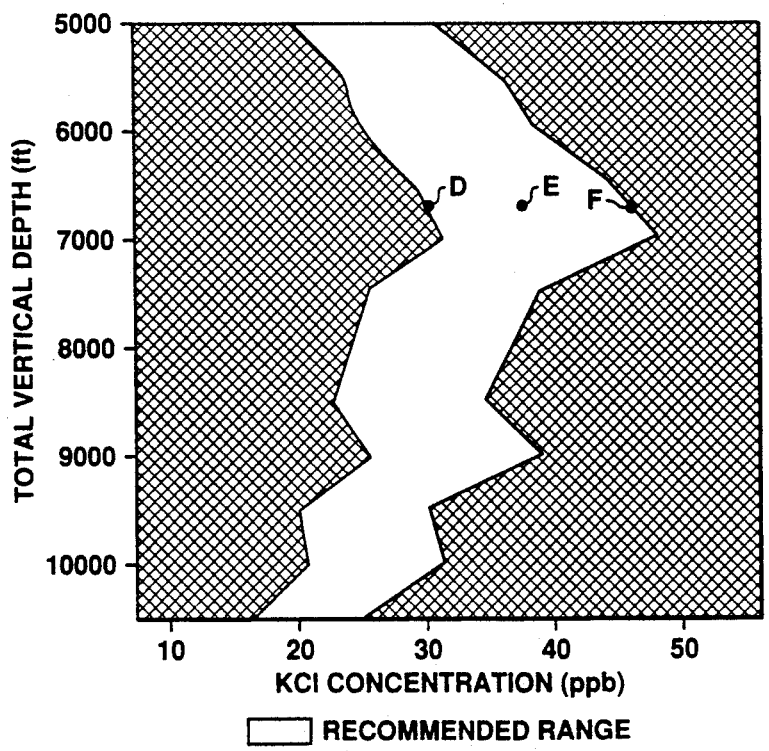
FIG. 8 is a graphical representation of potassium chloride concentrations obtained using prior art methods.
Figure 9:
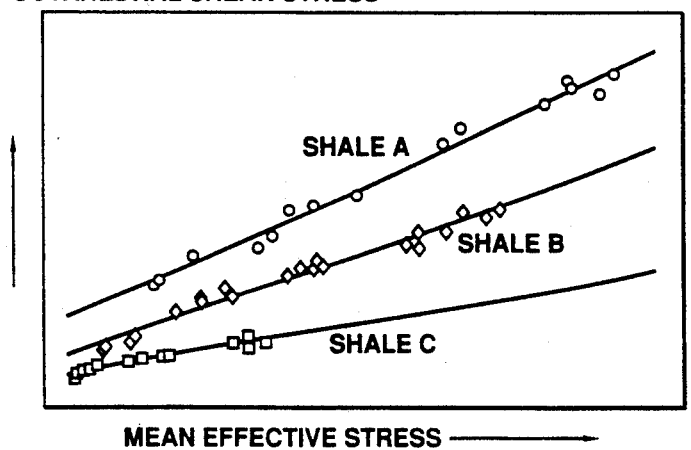
FIG. 9 shows the strength-mean effective stress relationship for different shales.
Figure 10:
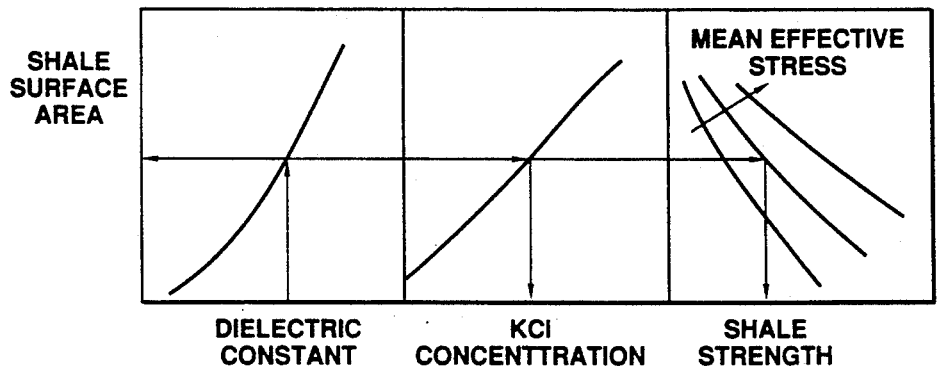
FIG. 10 is a schematic representation of a method according to this invention.

FIG. 8 presents potassium chloride concentration in the drilling mud. This is determined with prior art methods. Three points have been indicated, points D, E, and F. Point D represents the minimum KCl concentration level that is required to effectively inhibit shale swelling. Point E represents an intermediate KCl concentration at which shale hydration is inhibited. Point F represents the preferred upper range of KCl concentration that will effectively inhibit shale swelling.

Another shale strength-mean effective stress data base correlation according to the present invention is developed with ultrasonic velocity data. Ultrasonic velocity values for a particular field shale at depth are determined by prior art wellbore logging techniques and are then compared to the data base, e.g., in the laboratory, to obtain in situ shale strength.

Figure 11:
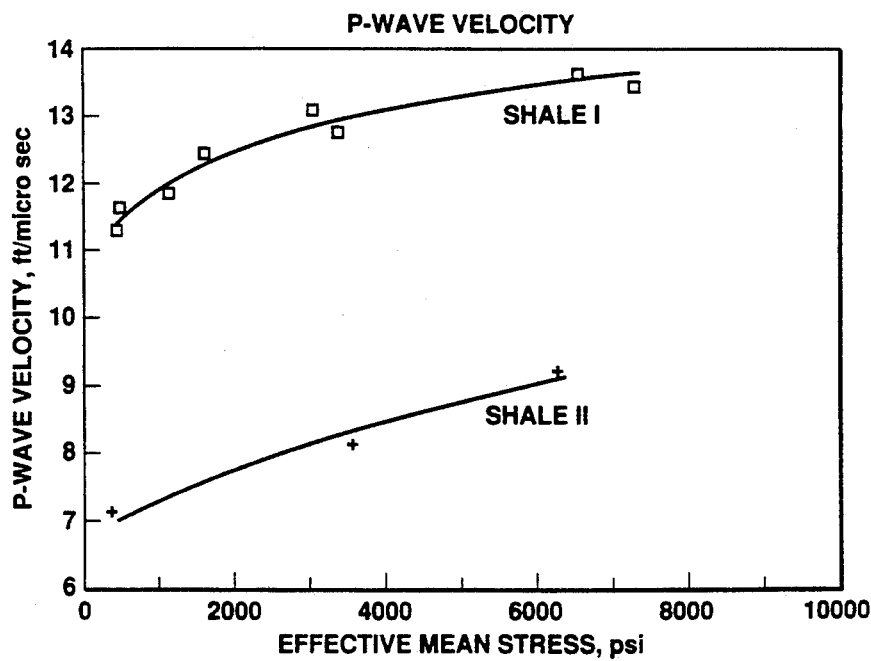
FIG. 11 presents a graph of a rock's ultrasonic velocity versus its mean effective stress.

Another remote-from-the-hole test data base correlation according to the present invention is developed for several different types of shales with data including ultrasonic velocity, surface area, and mean effective stress laboratory test measurements. The ultrasonic velocity values for different shales are functions of mean effective stress as derived by methods described in our copending application entitled "Apparatuses and Methods For Measuring Ultrasonic Velocities In Materials," producing results as shown in FIG. 11. Also, the surface areas of each of the shale types are determined and correlated with ultrasonic velocity and mean effective stress; e.g., in FIG. 11 Shale I has a low surface area and Shale II has a high surface area. Then in situ field pore pressure can be determined by combining field measurements of in situ (vertical) overburden stress, horizontal stress, ultrasonic velocity log data, and surface areas of shale cuttings. The in situ horizontal stress is determined by a prior art hydraulic leakoff (hydraulic microfracture) test. The in situ overburden stress is derived from prior art density log data. The mean effective stress is determined by comparing the surface area of the field shale cuttings and the log derived ultrasonic velocity from the zone of interest to the surface area-ultrasonic velocity-mean effective stress correlation from the laboratory test shale data base. The following method is used to obtain in situ pore pressure (u):

$$p' = [(\sigma_1 + 2\sigma_3/3] - u \quad (1)$$

where $p'$ = mean effective stress $\sigma_1$ = overburden stress $\sigma_3$ = horizontal stress $$\sigma_1 = \sum_{i=1}^{n} \gamma_i \Delta h_i$$

derived from the field density log where $\gamma_i$ = log density derived at each depth interval, $\Delta h_i$ $\sigma_3$ is determined from the extended hydraulic leakoff test p' is determined from the surface area—ultrasonic velocity—mean effective stress laboratory test data base correlation.

Then from (1):

$$u = [(\sigma' + 2\sigma_3)/3] - p' \quad (2)$$

The pore pressure (u) is determined by applying values for $\sigma'$, $\sigma_3$ and p' to equation (2).

In like manner, the following method is used to determine in situ field horizontal stress in an interval where the pore pressure has been measured or determined by prior art geophysical and drilling engineering methods by combining the value with the in situ shale surface area value determined from measurements of cuttings and by comparing the surface area to the shale surface area—ultrasonic velocity—mean effective stress laboratory stress data base correlation to obtain in situ mean effective stress (p'). The following method is then used to obtain in situ horizontal stress ($\sigma_3$):

The overburden stress ($\sigma_1$) is determined by using $$\sigma' = \sum_{i=1}^{n} \gamma_i \Delta h_i \text{ (see above)}$$

and $$\sigma_3 = \frac{3(p' + u) - \sigma_1}{2} \quad (3)$$

The in situ horizontal stress ($\sigma_3$) is determined by applying values for p', u and $\sigma_1$ to equation (3).

The copending application entitled "Methods and Apparatuses For Measurement of the Strengths, Pore Pressures, and Mechanical Properties of Low Permeability Geologic Materials," discloses how to obtain elastic properties, (e.g. Poisson's ratio, bulk modulus, Young's modulus, shear modulus, etc.) for a low permeability rock such as a shale and shows that elastic properties can be correlated with mean effective stress for such rock. The invention disclosed herein also shows that the elastic properties for different types of rocks can be correlated with mean effective stress and an index property (e.g. measured specific surface area).

In general, rock having lower specific surface area displays higher elastic properties, i.e. higher values for Young's modulus, bulk modulus, etc. and lower values for Poisson's ratio.

Figure 1:
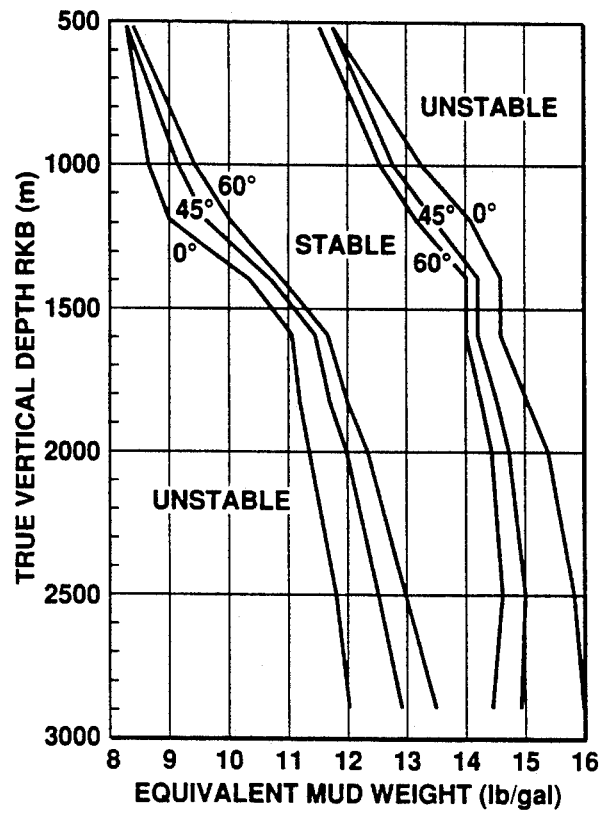
FIG. 1 is a graph of wellbore stability charts.
Figure 2:
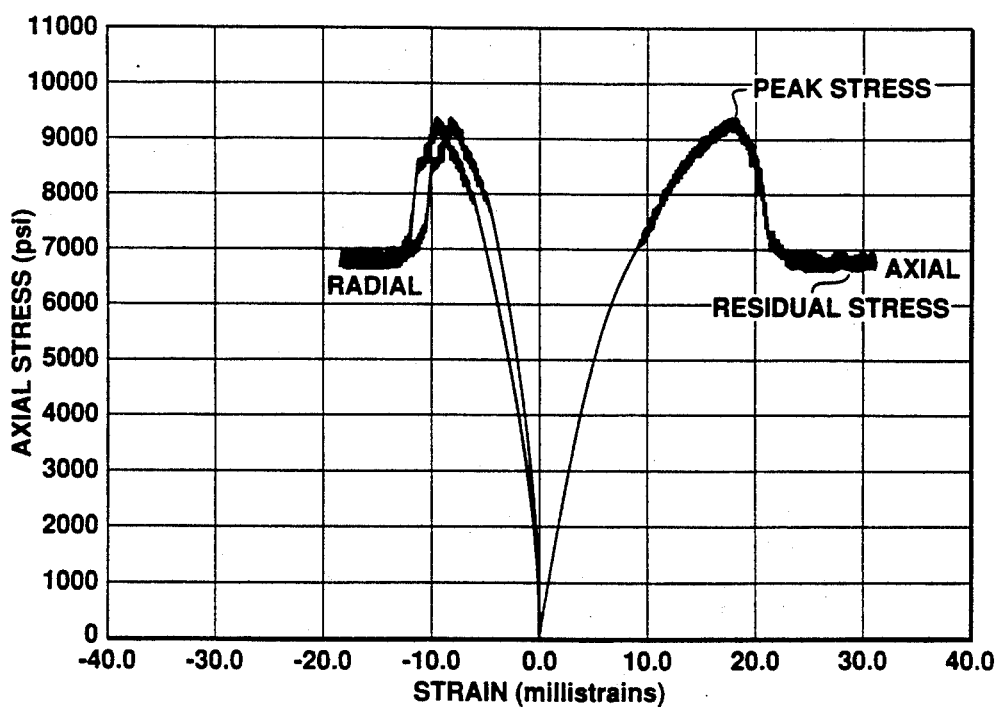
FIG. 2 is a graph of stress-strain curves for a low permeability shale.
Figure 3:
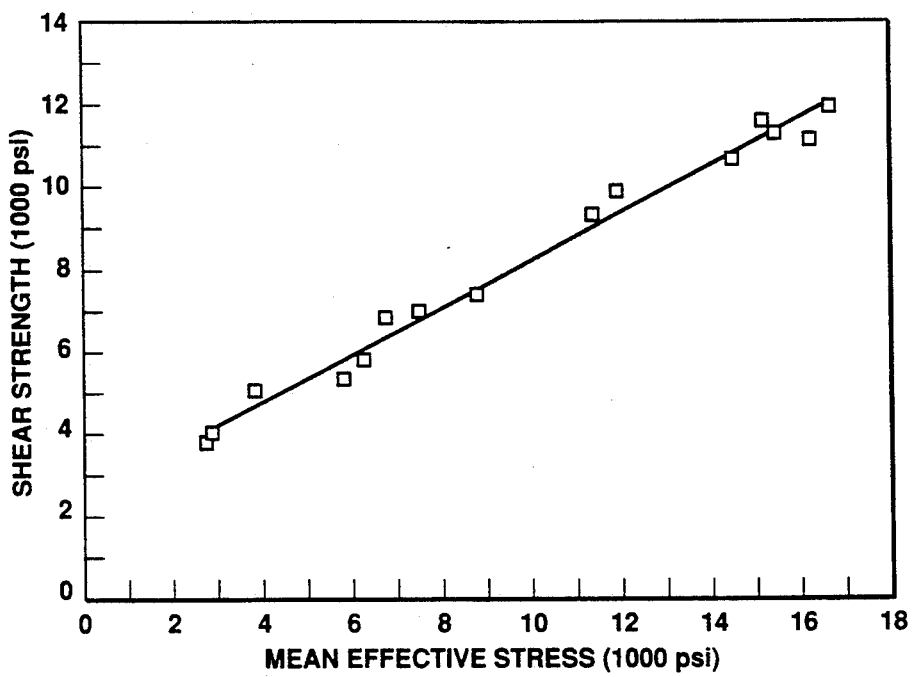
FIG. 3 is a graph of a failure criterion for a shale.
Figure 4:
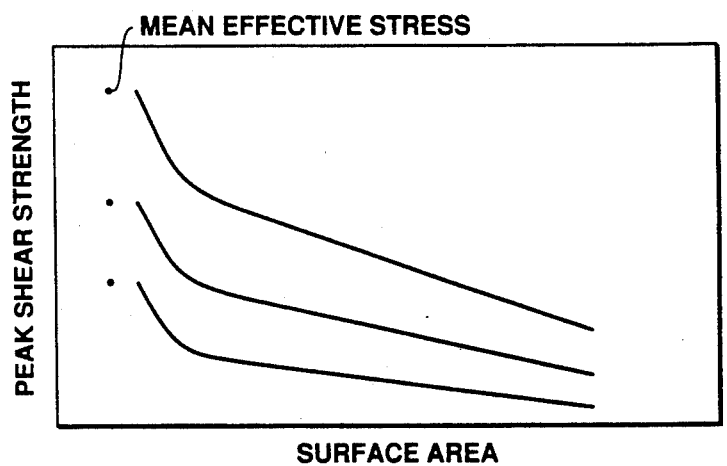
FIG. 4 is a graph of peak shale strength correlation according to the present invention.
Figure 5:
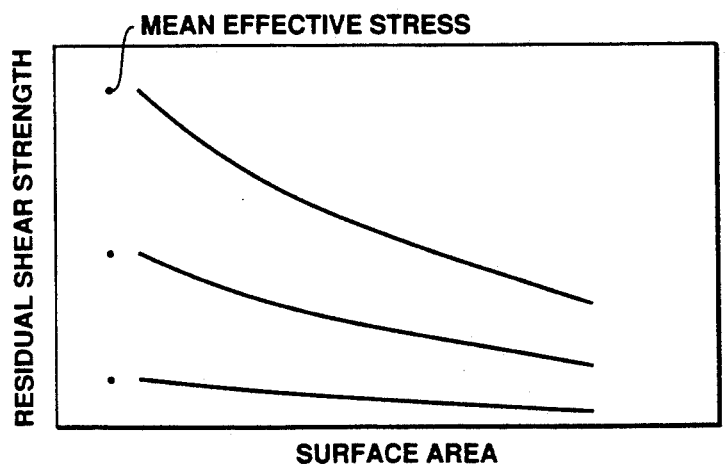
FIG. 5 is a graph of residual shale strength correlation according to the present invention.

The techniques described herein for determining strength of shale formation can also apply to solve other engineering problems related to construction work taking place in shale formations. Such applications include open pit mining, tunnel mining, road cut, tunnel construction, etc.) In these applications, a small amount of disturbed or undisturbed sample (approximately 10 grams) is collected from the representative shale formation. Then, the sample is analyzed using the EGME surface area technique or the dielectric constant method to obtain specific surface and measurements. The in situ strength of the formation then is estimated using the shale strength—surface area—mean effective stress correlations such as those presented in FIGS. 4 and 5. Alternatively, the sample is used to determine another index property. The in situ strength of the formation then is estimated using the shale strength—index property—mean effective stress correlation. Alternatively the sample is used to determine an index property that is then used to estimate elastic properties, such as a Poisson ratio and Young's modulus, using shale elastic property—index property—means effective stress correlations.

Knowing the in situ formation strength or elastic properties, engineering analyses can be conducted to obtain necessary design parameters. For example, in an open pit mining area, it is very important to determine the maximum slope angle that can be cut through the formation without causing slope failure. For this application, a small amount of out-crop sample will be collected and analyzed to obtain surface area estimates. Formation strength then is estimated using the shale strength—surface area—mean effective stress correlation. With formation strength, conventional slope stability analysis can be conducted to determine the maximum slope angle.

A preferred embodiment of the EGME shale surface area determination method is as follows:
1. Grind shale sample to pass 200 mesh screen
2. Cone, quarter and weigh 1.5 g sieved shale (<200 mesh) into 250 ml beaker.
3. Add 50 ml 30% hydrogen peroxide ($H_2O_2$) cautiously with occasional stirring. Let set overnight or until sample stops bubbling.
4. Filter through Whatman #50 filter paper using a stainless steel filter press at 100 p.s.i.
5. Rinse with 20 ml deionized water and filter. through cake. Repeat twice.
6. Allow filter cake sample to dry in air.
7. Grind cake and sieve (200 mesh).
8. Weigh 1.1 g shale into a dry, weighed 35 ml weighing dish.
9. Dry sample in a vacuum desiccator over granular phosphorous pentoxide ($P_2O_5$) for three hours. Release vacuum using room air passed through silica gel desiccant.
10. Reweigh sample immediately and calculate weight of dry sample.
11. Add 3 ml ethylene glycol monoethyl ether (EGME) to sample and swirl gently. Let set 30 minutes with lid on.
12. In a shallow dish add 75 g EGME to 50 g anhydrous calcium chloride pellets (4–20 mesh) ($CaCl_2$) and place in bottom of desiccator. Leave dish lid slightly ajar and surround dish with $CaCl_2$.
13. Place sample in desiccator and evacuate for 45 minutes. Seal desiccator and let set overnight.
14. Release vacuum using room air passed through silica gel.
15. Reweigh sample immediately and calculate gain as mg EGME/g dry sample.
16. Shale surface area ($m^2/g$)=

$$\frac{mg\ EGME/g\ dry\ sample}{0.329}$$

In conclusion, therefore, it is seen that the present invention and the embodiments disclosed herein are well adapted to carry out the objectives and obtain the ends set forth at the outset. Certain changes can be made in the method and apparatus without departing from the spirit and the scope of this invention. It is realized that changes are possible and it is further intended that each element or step recited in any of the following claims is to be understood as referring to all equivalent elements or steps for accomplishing substantially the same results in substantially the same or equivalent manner. It is intended to cover the invention broadly in whatever form its principles may be utilized. The present invention is, therefore, well adapted to carry out the objects and obtain the ends and advantages mentioned, as well as others inherent therein.

What is claimed is:

1. A method for measuring in situ pore pressure of a specimen low permeability rock, the method comprising obtaining a first rock sample from a first in situ location, measuring an index property of the first rock sample and obtaining a value for it, pressurizing the first rock sample triaxially by applying a load to it and a confining pressure, measuring continuously and recording the first rock sample's pore pressure while applying the load to it, applying the confining pressure to the first rock sample while applying the load to it, measuring and recording the ultrasonic velocities of the first rock sample at different pore pressures, determining the mean effective stress of the first rock sample at each different pore pressure, performing the previously-listed steps for a plurality of different rock samples from in situ locations, correlating ultrasonic velocity values and mean effective stress values with measured index property values for each sample and plotting a point on a graph for each such correlation, determining a curve that fits the plot of points representing each ultrasonic velocity versus its corresponding index property value and mean effective stress, measuring in situ ultrasonic velocities through the specimen, measuring the index property of the specimen, locating on the curve a point corresponding to the measured index property value and ultrasonic velocity value of the specimen, and then locating the mean effective stress value of the specimen corresponding to that index property value and ultrasonic velocity value, determining the in situ vertical stress of the specimen and horizontal stresses of the specimen, using the in situ mean effective stress from the curve, the in situ vertical stress and in situ horizontal stresses to determine the in situ pore pressure of the specimen.

2. The method of claim 1 wherein the index property is surface area.

3. A method for measuring in situ horizontal stress of a low permeability formation, the method comprising obtaining a first rock sample from a first in situ location, measuring an index property of the first rock sample and obtaining a value for it, pressurizing the first rock sample triaxially by simultaneously applying a load to it and a confining pressure, measuring continuously and recording the first rock sample's pore pressure while applying the load to the first rock sample, applying the confining pressure to the first rock sample while applying the load to it, measuring and recording ultrasonic velocities through the first rock sample at different pore pressures, determining the mean effective stress of the first rock sample at each different pore pressure, performing the previously-listed steps for a plurality of different rock samples from the in situ location, correlating ultrasonic velocity values and mean effective stress values with measured index property values for each sample and plotting a point on a graph for each such condition, determining a curve that fits the plot of points representing each ultrasonic velocity versus its corresponding index property value and mean effective stress value, measuring the in situ ultrasonic velocity through an in situ specimen low permeability rock, measuring the index property of the in situ specimen, locating on the curve a point corresponding to the measured index property value of the in situ specimen and ultrasonic velocity value, then locating the mean effective stress value corresponding to that index property and ultrasonic velocity value, determining the in situ vertical stress and pore pressure of the in situ specimen, and using the in situ means effective stress from the curve, the in situ vertical stress and pore pressure to determine the in situ horizontal stress of the in situ specimen.

4. The method of claim 3 wherein the index property is surface area.

* * * * *